United States Patent [19]
Toomim et al.

[11] Patent Number: 5,995,857
[45] Date of Patent: Nov. 30, 1999

[54] BIOFEEDBACK OF HUMAN CENTRAL NERVOUS SYSTEM ACTIVITY USING RADIATION DETECTION

[76] Inventors: I. Hershel Toomim, 3710 S. Robertson Blvd., Culver City, Calif. 90232; Robert C. Marsh, 8 Kiki Pl., Pacific Palisades, Calif. 90272

[21] Appl. No.: 08/883,745

[22] Filed: Jun. 27, 1997

Related U.S. Application Data

[60] Provisional application No. 60/015,369, Jul. 1, 1996.

[51] Int. Cl.$^6$ ............................................. A61B 5/00
[52] U.S. Cl. ..................... 600/322; 600/333; 600/340; 600/504; 128/905
[58] Field of Search ................... 600/544, 545, 600/322, 323, 333, 340, 473, 476, 407, 454, 504; 128/905

[56] References Cited

U.S. PATENT DOCUMENTS

| | | | |
|---|---|---|---|
| 4,270,545 | 6/1981 | Rodler | 600/407 |
| 4,515,165 | 5/1985 | Carroll | 128/664 |
| 4,859,057 | 8/1989 | Taylor et al. | 600/323 |
| 5,062,431 | 11/1991 | Potter | 128/665 |
| 5,127,407 | 7/1992 | Tan | 128/633 |
| 5,167,230 | 12/1992 | Chance | 600/323 |
| 5,174,298 | 12/1992 | Dolfi et al. | 128/665 |
| 5,187,672 | 2/1993 | Chance et al. | 364/550 |
| 5,217,013 | 6/1993 | Lewis et al. | 600/342 |
| 5,239,185 | 8/1993 | Ito et al. | 250/573 |
| 5,309,907 | 5/1994 | Fang et al. | 128/633 |
| 5,402,778 | 4/1995 | Chance | 128/633 |
| 5,433,196 | 7/1995 | Fiat | 600/409 |
| 5,441,054 | 8/1995 | Tsuchiya | 128/665 |
| 5,482,034 | 1/1996 | Lewis et al. | 600/323 |
| 5,603,322 | 2/1997 | Jesmanowicz et al. | 600/410 |
| 5,685,305 | 11/1997 | Moonen et al. | 324/306 |
| 5,694,939 | 12/1997 | Cowings | 600/544 |

OTHER PUBLICATIONS

Mathew et al., "Biofeedback Control of Skin Temperature and Cerebral Blood Flow in Migraine," Headache, pp. 19–28, Jan. 1980.

McGrady et al., "Effect of Biofeedback–Assisted Relaxation on Migraine Headache and Changes in Cerebral Blood Flow Velocity in the Middle Cerebral Artery," Headache, pp. 424–428, Jul. 1994.

Wauquier et al., "Changes in Cerebral Blood Flow Velocity Associated With Biofeedback–Assisted Relaxation Treatment of Migraine Headaches are Specific for the Middle Cerebral Artery," pp. 358–362, Jun. 1995.

Hoshi and Tamura, Multichannel near–infrared optical imaging of brain activity, pp. 1842–1846, Oct. 1993, Journal of Applied Physiology.

(List continued on next page.)

*Primary Examiner*—Eric F. Winakur

[57] ABSTRACT

Apparatus and method for biofeedback of human central nervous system activity using radiation detection. This invention uses radiation from the brain resulting either from an ingested or injected radioactive material or radio frequency excitation or light from an external source impinging on the brain. The radiation is measured by suitable means and is made available to the subject on which the measurement is being made for his voluntary control. The measurement may be metabolic products of brain activity or some quality of the blood, such as its oxygen content. One such system utilizes red and infrared light to illuminate the brain through the translucent skull and scalp. Absorption and scattering of incident radiation depends on the degree of oxygen saturation of the blood in the illuminated tissue. The relationship of the returned scattered and absorbed light intensities can be obtained and displayed via a suitable display of sound, graphics or both so that a human being included in the feedback system can attempt to vary the display and thereby control the actual brain blood oxygenation at will. Control of brain blood perfusion is so quickly mastered that most subjects require less than 5 minutes to gain control.

21 Claims, 7 Drawing Sheets

OTHER PUBLICATIONS

Chance, Kang and Sevick, Photon diffusion in breast and brain: spectroscopy and imaging, pp. 9–13 Oct. 1993, Optics and Photonics News.

Gratton, Fabiani and Corballis, Can we measure correlates of neuronal activity with non–invasive optical methods, pp. 53–62, 1997, Advanced Experimental Medical Biology.

Takatani and Ling, Optical oximetry sensors for whole blood and tissue, pp. 347–357, 1994, IEEE Engineering in Medicine and Biology.

Kurth, Steven, Benaaron and Chance, Near–infrared monitoring of the cerebral circulation, pp. 163–170 1993, Journal of Clinical Monitoring.

Gratton, Maier, Fabiani, Mantulin and Gratton, Feasibility of intracranial near–infrared optical scanning, pp. 211–215, 1994. Psychhhophysiology.

Gratton, Corbalis, Cho, Fabiani and Hood, Shades of gray matter: noninvasive optical images of human brain responses during visual stimulation, pp. 505–509, 1995, Psychophysiology.

Gratton and Corballis, Removing the heart from the brain; compensation for the pulse artifact in the photon migration signal, pp. 292–299, 1995, Psychopysiology.

BIOFEEDBACK OF HUMAN CENTRAL NERVOUS SYSTEM ACTIVITY USING RADIATION DETECTION

CROSS-REFERENCE

The Applicants claim the benefit of their prior Provisional Patent Application, serial No. 60/015,369, filed Jul. 1, 1996.

BACKGROUND OF THE INVENTION

1. Field of the Invention

The present invention relates to a method and equipment for biofeedback of alterable characteristics of the brain with the objective of altering blood flow and encouraging vascular growth in a manner conducive to the mental health of a human being.

2. Brief Description of the State of the Art

With the advent of SPECT, PET and fMRI, blood flow in various brain areas is increasingly being correlated with various brain disorders such as Attention Deficit Disorder (ADD), Schizophrenia, Parkinson's Disease, Dementia, Alzheimers Disease, Endogenous Depression, Oppositional Defiant Disorder, Bipolar Disorder, memory loss, brain trauma, Epilepsy and others.

These disorders are, at present, mainly treated with psychoactive drugs and or psychotherapy. Such treatments are marginally effective. The drugs require continuous treatment schedules and have serious side effects such as Tardive Diskinesia, sleep disruption, drowsiness, dullness, skin disorders and digestive interference. Psychotherapy is of limited usefulness in these disorders and is very expensive.

Previous brain blood flow measurement techniques have required injection of radioactive materials into the blood stream or irradiation of brain tissue with radio frequency power. These are, at present, slow and expensive, requiring minutes to achieve a measurement. Consequently, at present, many important clues to brain operation are completely obscured. See "Interactions Between Electrical Activity and Cortical Microcirculation Revealed by Imaging Spectroscopy: Implications for Functional Brain Mapping", Malonek, D. and Grinvad, A., Science, May 26, 1997, pp. 551–554. Continued research and development are making inroads on these obstacles and it is anticipated that the radioactive tracer and radio frequency irradiation techniques will eventually become useful for biofeedback.

Research has demonstrated that low frequency electrical activity of the brain, as measured by the EEG, is negatively correlated with brain blood flow. ADD as well as many other brain disorders are characterized by excessive, slow wave activity and below normal blood flow to one or more brain areas. See "Cerebral Glucose Metabolism in Adults with Hyperactivity of Childhood Onset", Zametkin, A. J. et al., New England Journal of Medicine, Sep. 15, 1990, pp. 1361–1366.

In recent years Electroencephalographic (EEG) Biofeedback has been used for treating brain disorders with considerable success. A limited course of treatment produces lasting effects. EEG Biofeedback has made great strides in the treatment of some of these problems. Attention Deficit Disorder (ADD) is on outstanding example. The EEG Biofeedback technique makes non-invasive measurements of brain electrical activity, modifies them to enhance important characteristics and attempts to present the result in a readily understandable form to the patient so that the he can modify the EEG in a healthful direction.

EEG Biofeedback is difficult to utilize because of the required multiple electrodes and the required skin preparation for each electrode. See "Muscles Alive", J. V. Basmajian and C. J. Deluca, Williams and Wilkins, Baltimore, pp. 22–23. It is also sensitive to artifacts due to eye and muscle movement. This is especially troublesome near the prefrontal cortex, an important brain area involved in executive functions, planning, and working memory. The complex electrical signals obtained are ambiguous and represent many simultaneous events. They are difficult for the trainee to interpret and require many sessions before control is learned. The cost of present day EEG Biofeedback equipment, the skill required to operate it, and the total required treatment time has made this technique so costly that only a small proportion of the estimated eleven million handicapped people in the United States who need access to this technology can afford it.

Development of a low cost non-invasive brain blood flow monitor represents a great improvement in the field of biofeedback and provides, for the first time, an easily used, safe method of treating many devastating brain disabilities, satisfying a long felt need of the mental patient and the mental health professional.

SUMMARY OF THE INVENTION

This invention uses radiation from the brain resulting from: an ingested or injected radioactive material, such as is used in the PET, SCAN or SPECT systems; radio frequency excitation, such as used in MRI; or energy from an external source impinging on the brain. The returned radiation is measured by suitable means and is made available to the subject on which the measurement is being made for his voluntary control. The measurement may relate to metabolic products of brain activity or some quality of the blood such as its oxygen content. Depending on the technique used, the length of path that the radiation travels may or may not be used to localize the subject brain tissue of implementation and need to be compensated. This affects the complexity of calculation that needs to be performed in order to correlate the measured radiation to the metabolic products or quality of the blood and to present this measurement in a meaningful way.

One such system uses reflected and scattered light from an incident light source to assess the brain blood oxygenation. With this system response is immediate. It has the advantage of convenience and simplicity: no skin preparation or radio active tracer material injection is required.

This form of the present invention allows simple, non-invasive, low cost measurement and control of brain blood flow. It provides real time information in small fractions of a second and requires only donning of a headband with a light source and a photoelectric amplifier coupled to an electronic sound or visual display. No injection or skin preparation is necessary. This invention uses non-ionizing and non-invasive radiation, traversing the skull and overlying tissues, to illuminate the brain. See "Near Infrared Monitoring of the Cerebral Circulation", Kurth, C. D., Steven, J. M., Benaron, D., Chance B., Journal of Clinical Monitoring, vol. 9, no. 3 (1993). Reflected and scattered radiation, as modified by blood flow in the brain, is sensed at the scalp, interpreted, and presented to the trainee for control.

This form of the present invention utilizes the techniques of oximetry using red and infra-red light to illuminate the brain through the translucent skull and scalp. Absorption and scattering of incident radiation depends on the degree of oxygen saturation of the blood in the illuminated tissue and the wavelength of the illumination. By alternately illuminating the tissue with red and infrared light, the relationship of the returned scattered and absorbed light intensities can be obtained. The relationship can be difference, ratio or any other meaningful calculation, however ratio is preferred. Wavelengths are chosen to maximize the difference in response to oxyhemoglobin and deoxyhemoglobin in the red and in the infrared regions. The ratio is displayed via a suitable display of sound, graphics or both so that a human being included in the feedback system can attempt to vary the display and thereby control the actual brain blood oxygenation at will.

Ratio is, to a first approximation, independent of the depth of penetration of the examined tissue, the brightness of the light and the length of path that the light travels. This is an important consideration in removing interference from the composition and thickness of the scalp, hair, skull and meninges. The system is responsive to the average density of blood in the examined tissue which is dominated by the capillary system so that arteries and arterioles are of negligible importance to the measurement.

This technique offers great flexibility in optimizing brain blood flow to selected brain areas and has not been used heretofore in the biofeedback mode nor has it been used for voluntary control of brain blood perfusion. Control of brain blood perfusion is so quickly mastered that most subjects require less than 5 minutes to gain control when presented with ongoing measures of brain blood flow. This is in great contrast to the difficult task of learning to control the EEG to optimize brain improvement which requires 6 to 10, 45 minute sessions.

Although alternate illumination with the two radiation wavelengths is described above, it is also reasonable to illuminate with both simultaneously and to separate the returned light by means of filters or other spectrophotometric techniques.

An appreciation of the other aims and objectives of the present invention and an understanding of it may be achieved by referring to the accompanying drawings and description of a preferred embodiment.

DETAILED DESCRIPTION OF THE PREFERRED EMBODIMENT

Figure 1:
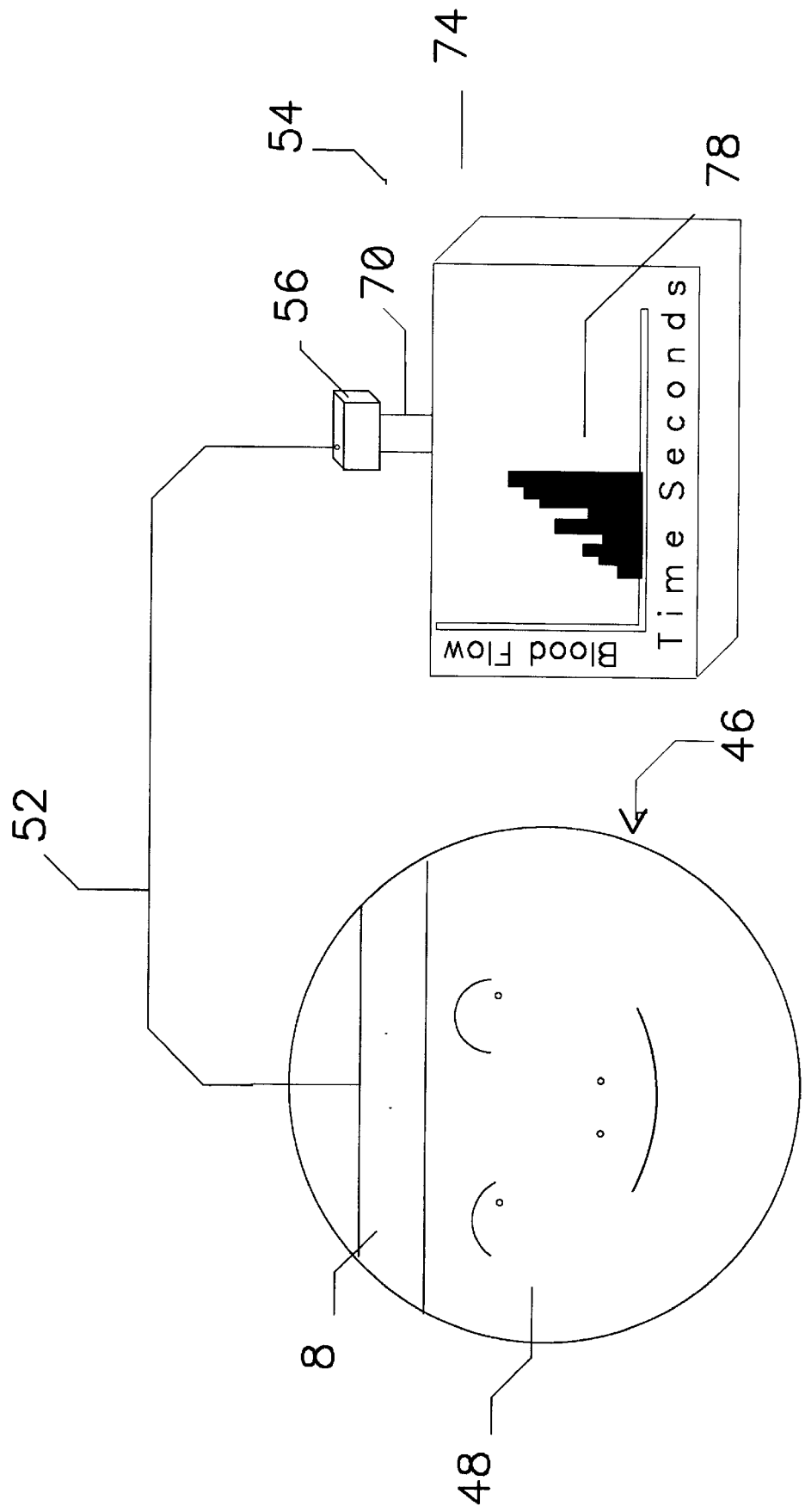
FIG. 1 illustrates the general principle of this invention.

FIG. 1 illustrates the general principle of this invention 54. FIG. 1 shows an individual 46 wearing a detector 8 attached to his head 48. The detector 8 is responsive to any radiation modified by the particular brain characteristic it is desired to study. Such radiation is produced in response to energy from an energy source. Such an energy source may be:

1) radioactive material, selected for a specific brain characteristic, inhaled, ingested, or injected into the individual 46;
2) radio frequency excitation tuned to the precession frequency of an atom it is desired to influence; or
3) one or more light sources which can illuminate brain tissue with a wavelength or wavelengths chosen for susceptibility to the particular brain characteristic it is desired to influence.

On FIG. 1 the detector 8 is shown attached directly to the head 48. However, the detector 8 need not be so attached and may be a camera, or other kind of detector 8 responsive to the radiation of interest, at a distance from the head 48. One cable 52 connects the detector 8 to an electronic processor 56 and a second cable 70 connects the processor 56 to a suitable display module 74. The electronic processor 56 typically includes a computer, which is not separately illustrated. The electronic processor 56 can either be analog or digital. An analog processor 56 can do the desired calculations continuously. A digital calculator 56 with memory can do the desired calculations serially. Preferably, the display 78 is visual but an audible, audio/visual or tactile display 78 could easily be used. While wires, cables, printed or flexible circuits, and connectors are the most usual methods of connecting electrical components, it will be recognized by those familiar with the art to which this invention pertains that connection of electrical components can also be done by wireless means, such as infrared or radio-frequency. Furthermore, while use of a processor 56 is preferred, it will be recognized by those familiar with the art to which this invention pertains, that, if the display 78 is sophisticated enough, such as a modern oscilloscope, this invention may be practiced without the processor 56.

Figure 2:
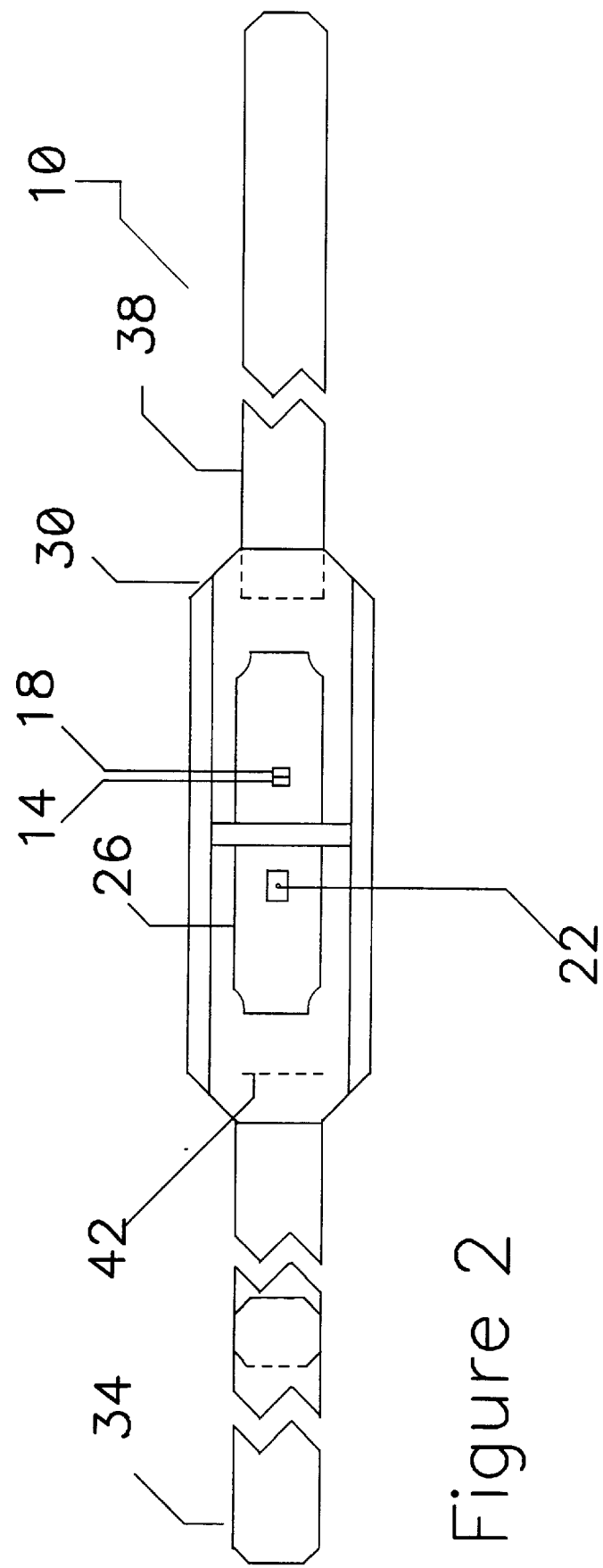
FIG. 2 illustrates the preferred irradiation/detection subsystem of this invention at its full length, viewed from the inside.

The preferred characteristic is the relationship of oxygenated hemoglobin to deoxygenated hemoglobin. FIG. 2 illustrates the preferred irradiation/detection subsystem 10 of this invention, viewed from the inside. This subsystem 10 is essentially a positioning means for the preferred radiation sources and detectors for carrying out this invention 54. The heart of the preferred subsystem 10 is a subassembly 12 of a dual light source 14, 18 and photo amplifier 22 mounted on a flexible membrane 26. The membrane 26 is a printed flexible circuit for mounting and interconnecting the light sources 14, 18 and the photo detector 22. The light sources 14, 18 are mounted as close together as possible: orientation is immaterial. While the preferred irradiation/detection subsystem 10 includes two individual light sources 14, 18, it will be recognized by those familiar with the art to which this invention pertains that light energy could be provided by other means such as one or more light pipes. Moreover, the light could be provided with a broad range of wavelengths and filters to limit the wavelength or wavelengths to that or those of greatest application.

In the preferred subsystem 10, this subassembly 12, in turn, is mounted on a band 30 which can easily mold to the contours of the head 48. The band 30 must be at least partially opaque to external radiation to protect the photo sensor 22 from external light sources. The band 30 can be made of neoprene or similar elastomer adapted to secure around the head 48. A barrier layer, not illustrated, can be placed over the membrane 26 in the interests of cleanliness. If such a barrier layer is used electrodes, not illustrated, are necessary for grounding. The preferred fastening method is strips of hook 34 and loop 38 fastener attached to the ends of the band 30. A connector 42, located on the membrane 26 away from the band 30, enables connection of the dual light source 14, 18 and photo amplifier 22 to external electronics. While wires, cables, printed or flexible circuits, and connectors are the most usual methods of connecting electrical components, it will be recognized by those familiar with the art to which this invention pertains that connection of electrical components can also be done by wireless means, such as infrared or radio-frequency.

The first light source 14 is preferably a red light emitting diode (LED) radiating in the range of 650 to 700 nm with 660 nm being the preferred wavelength. The first light source 14 is a Stanley Electric model BR1102W or equivalent. The BR1102W outputs 3 mW at an excitation current of 20 ma. The second light source 18 is preferably an infrared LED radiating at a wavelength in the range of 800 to 1000 nm with 920 nm being the preferred wavelength. The second light source 18 is a Stanley Electric model AN1102W or equivalent. The AN1102W outputs 3 mW at an excitation current of 20 ma. These wavelengths are chosen to maximize the difference in response to oxyhemoglobin and deoxyhemoglobin in the red, 650 to 700 nm range, and to maximize the difference in response to deoxyhemoglobin and oxyhemoglobin in the infrared, 800 to 1000 nm range.

The photo sensor 22 maximally responds in the limited range of the chosen radiation wavelengths. The photo sensor is a Burr Brown model OPT 101R or equivalent. It discriminates against other unused wavelengths below 600 nm and above 960 nm by means of built in wavelength filters.

The depth of penetration and intensity of the returned light depends on the separation between the closely spaced light sources 14, 18 and the photo sensor 22 as well as on the available light energy. To insure adequate returned light intensity and to reach the cerebral cortex at a depth of approximately 1.5 cm, the distance between the light sources 14, 18 and the photodetector 22, using 20 ma excitation current, should be less than 3.5 cm and greater than 2 cm. The preferred separation is 3 cm. The use of laser light sources, when they become available, will allow greater separation and penetration depth. The subsystem 10 can be designed to examine fairly large or extremely small volumes of tissue depending on the portion of the brain in which it is desired to modify blood flow.

There is a limit to the light energy that can be applied to tissue without causing damage. However, higher power light sources 14, 18 can alternatively be used without causing damage, providing the exposure times are very short, e.g. of the order of picoseconds. With such a pulsed light source system, the time of flight to determine position and color of the returned radiation can be measured.

While FIG. 2 illustrates the preferred construction of the subsystem 10, it will be recognized by those familiar with the art to which this invention pertains that alternate subsystems can be conceived and constructed. All that is necessary is that the band 30 be at least partially opaque, fasten securely to the head 48, and carry on its internal surface the two light sources 14, 18 and light detector 22 which must be separated from, yet electrically connected to, each other as described above. Furthermore, it will be recognized that a positioning means for the preferred embodiment of this invention 54 may be an array of radiation sources 14, 18 and detectors 22 adhesively attached to the head 48. Alternatively, the positioning means may be a cap with light pipes for the radiation sources 14, 18 and multiple detectors 22 mounted on its inner surface.

Figure 3:
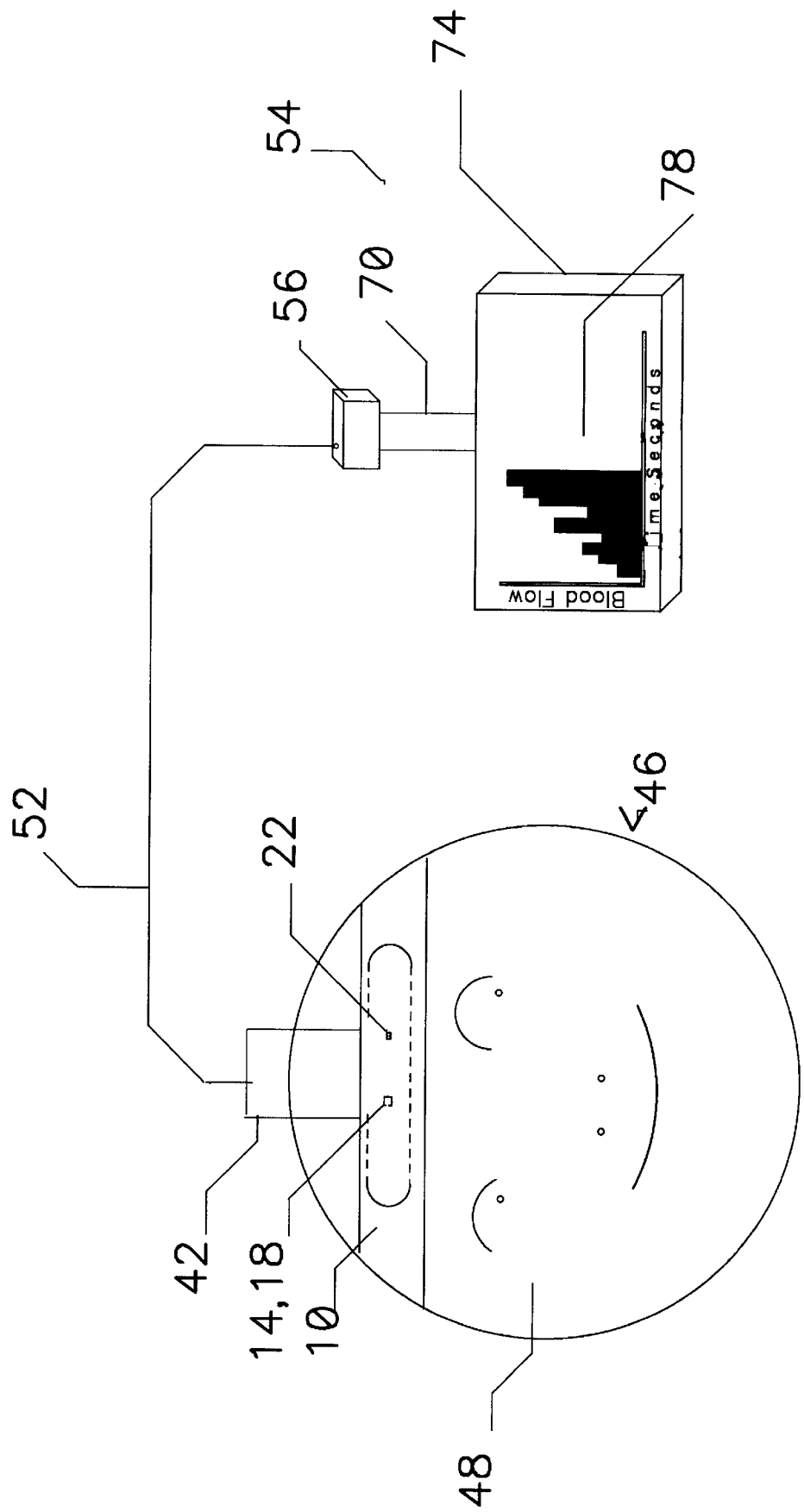
FIG. 3 shows a trainee hooked up to the preferred irradiation/detection subsystem of this invention, which is connected to an electronic processor and suitable display.

FIG. 3 shows an individual 46 wearing the headband 10 illustrated in FIG. 2 attached to his head 48. While the headband 10 is shown with the light sources 14, 18 and detector 22 adjacent to the forehead 50, it can be worn in any convenient position around the head 48. One cable 52 connects the headband electronics 14, 18, 22 via the connector 42 to an electronic processor 56 and a second cable 70 connects the processor 56 to a suitable display module 74. The electronic processor 56 typically includes a computer, which is not separately illustrated. The electronic processor 56 can either be analog or digital. An analog processor 56 can do the desired calculations continuously. A digital calculator 56 with memory can do the desired calculations serially. The connected parts illustrated on this figure comprise the preferred embodiment of this invention 54. In the preferred embodiment, the display 78 is visual but an audible, audio/visual or tactile display 78 could easily be used. In the preferred embodiment, the processor 56 alternately drives the light sources 14, 18 to illuminate the brain with the selected light wavelengths, interprets the photoelectric intensities returned and presents a display 78 to the trainee 46 to guide his efforts to enhance or decrease his brain blood flow. Alternatively, light from the light sources 14, 18 could be "turned on and off" by Kerr cells, or liquid crystal or equivalent devices. When the headband 10 is attached to the trainee's head 48 as illustrated in FIG. 3, the dual light sources 14, 18 are directed at his brain and the light sensitive detector 22 receives reflected and scattered light from his brain.

While FIGS. 1, 2 and 3 all illustrate an invention 54 having separate components at a distance from each other and being connected together, it should be recognized that the whole invention 54 could be built into one integrated device. For example, the invention 54 could be built into a cap with the display module 74 built into the underside of the visor.

Figure 4:
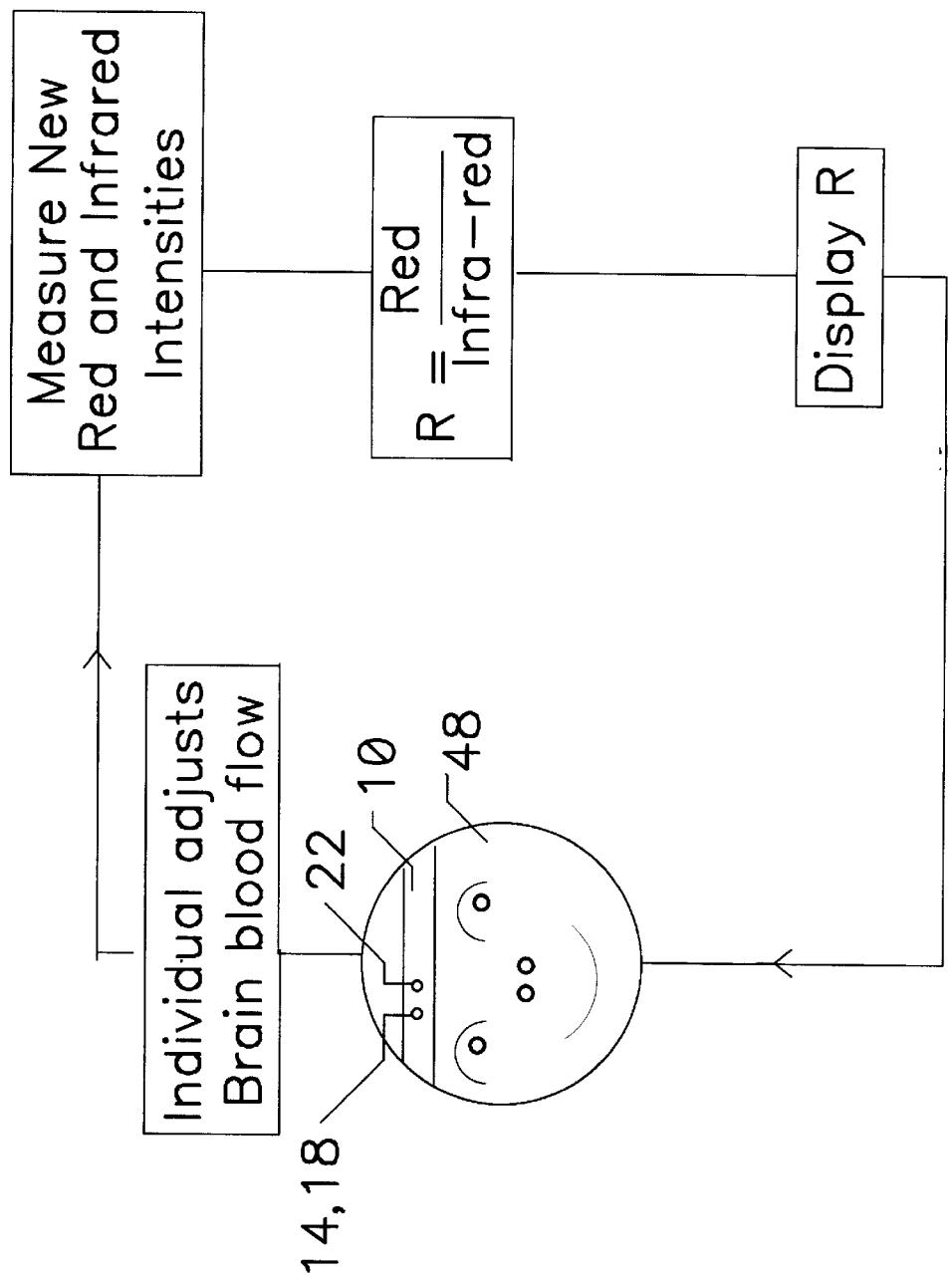
FIG. 4 is a logic flow diagram for the preferred embodiment of this invention.

FIG. 4 is a logic flow diagram for the preferred embodiment of this invention 54. The processor:

1) alternately illuminates the brain of the trainee 46 with two light wavelengths;

2) measures the returned light of each wavelength;

3) compares returned light intensity to determine which is red and which is infrared (infrared is always the larger);

4) calculates the red to infrared light intensity ratio R which approximates the oxyhemoglobin to deoxyhemoglobin ratio; and 5) displays the result R with sufficient sensitivity for control by the trainee.

In the preferred embodiment, as described above, each light source 14, 18 is alternately illuminated. However, it is conceivable to illuminate both light sources 14, 18 simultaneously and to separate the returned light by means of filters or other spectrophotometric techniques.

Figure 5:
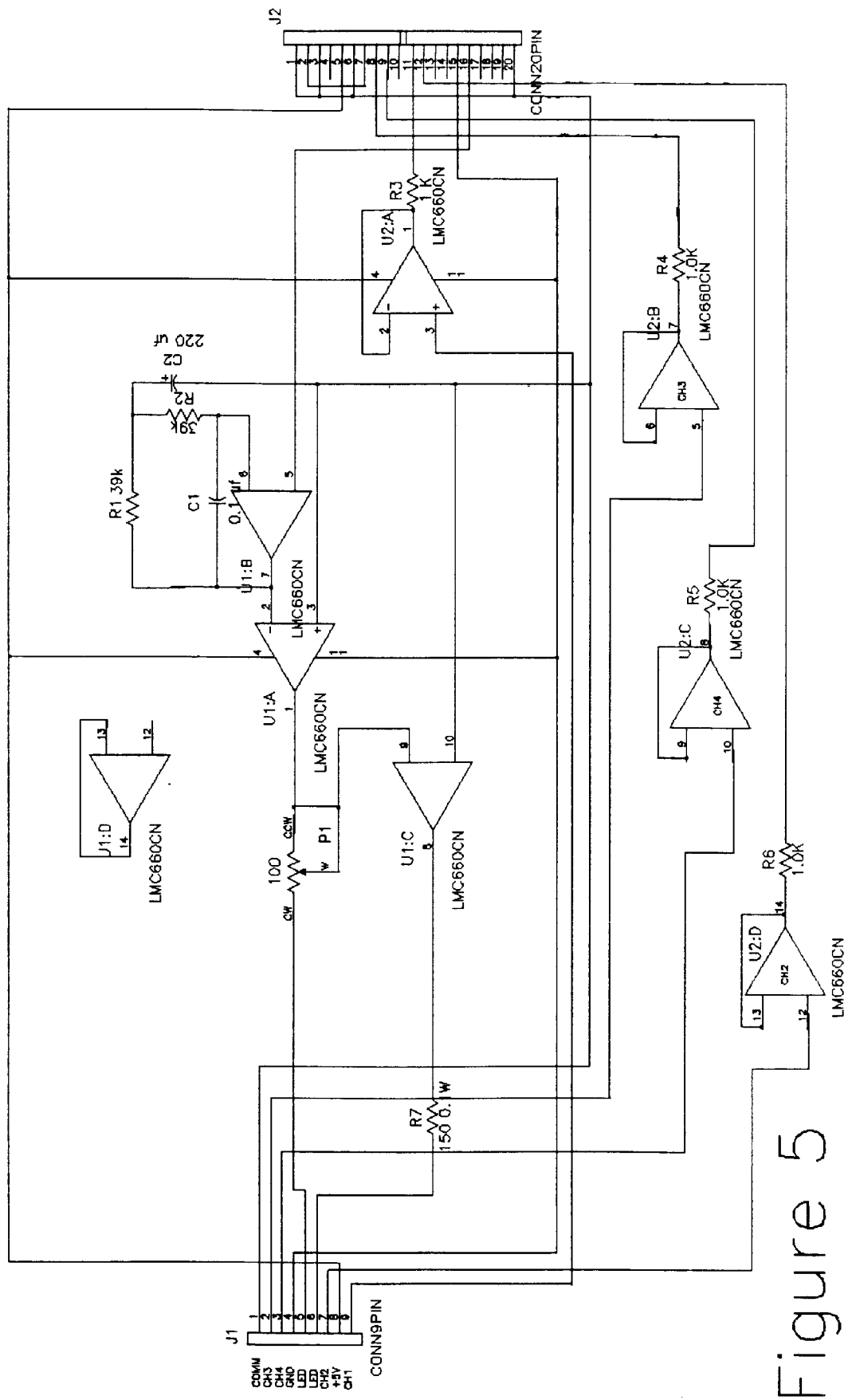
FIG. 5 is a diagram of the electronic circuitry required to drive the alternating light sources and to amplify the returned signal for processing by the display unit of the preferred embodiment of this invention.

FIG. 5 is a diagram of the electronic circuitry required to drive light sources 14, 18 alternately and to amplify the returned signal for display on the display unit 74. The preferred embodiment of the invention excites the two light sources 14, 18 alternately and a computer program calculates the ratio of the two received intensities for display. The circuit of FIG. 5 receives a timing square wave of 17 hz from the host computer on pins 6 and 16 of connector J2. At the transition times of the square wave, the computer reads the output light signal on pin 11 of connector J2. Pins 4 and 8 of connector J1, supply power to the photo amplifier 22 of the headband 10. Pins 5 and 6 of connector J1 supply a square wave of current to the opposing polarity connected light sources 14, 18. Pin 9 of connector J1 carries the photo amplifier 22 output to the buffer amplifier U4C.

Pins 1, 2, and 3, of connector J1 collect signals from added photo sensors 22 on the headband (not shown) to achieve multichannel capability. In the preferred embodiment the red light is always lower in intensity than the infrared light. This characteristic is used by the computer program to sort the returned signals for calculation and display of the oxyhemoglobin to deoxyhemoglobin ratio. This ratio follows the blood requirements of the active brain tissue being monitored.

An equally viable system excites the two sources 14, 18 simultaneously. It uses a dual photo receiver 22 with red and infrared filters and thereby separates the two wavelengths for calculation of the relationship to be displayed.

Figure 6:
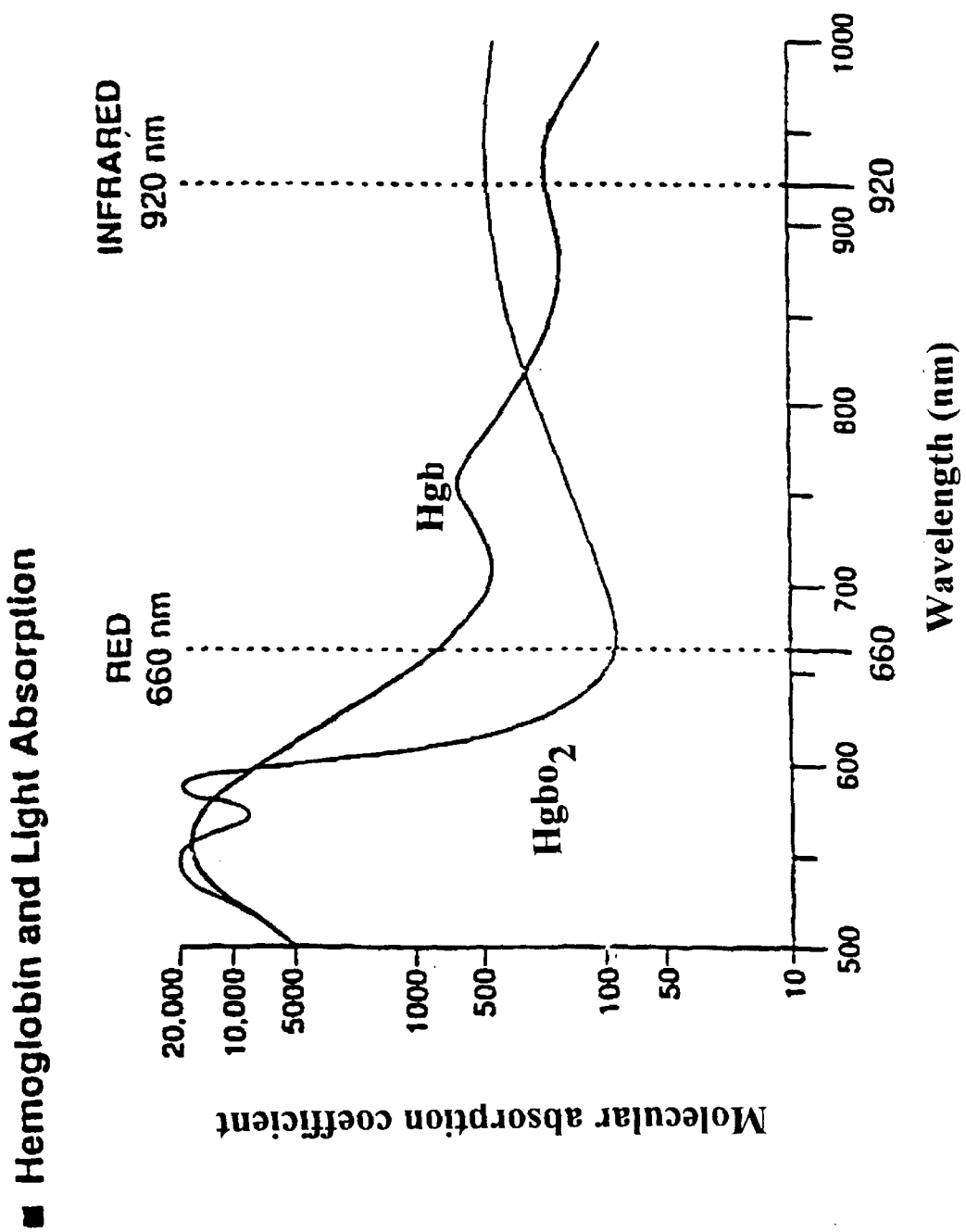
FIG. 6 shows the relationship between wavelength and light absorption of deoxyhemoglobin and oxyhemoglobin.
Figure 7:
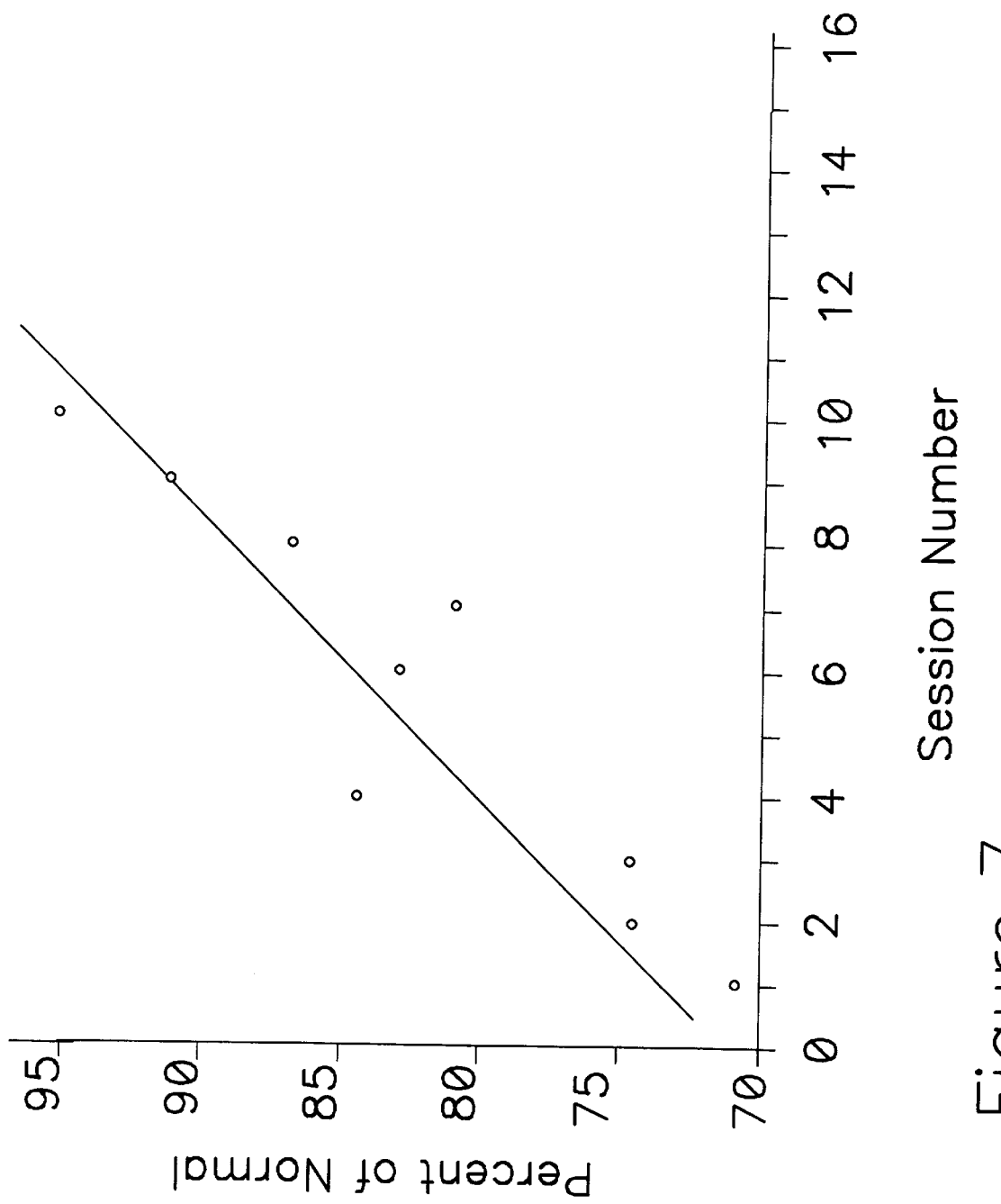
FIG. 7 shows the increases in initial brain blood flow in a extremely depressed, suicidal patient at each of 10 half hour treatments using of the preferred embodiment of this invention.

FIG. 6 shows the relationship between wavelength and light absorption of deoxyhemoglobin (Hgb) and of oxyhemoglobin ($HgbO_2$). It can be seen that the curves separate from about 600 to 775 nm and above about 825 nm. However, the frequencies where the greatest differences occur are 660 nm and 920 nm. That is why the wavelengths for the light sources 14, 18 are chosen to be 650 to 700 nm with 660 nm being the preferred wavelength and 800 to 1000 nm with 920 nm being the preferred wavelength Experimental Results FIG. 7, shows the effect of blood flow training. Each succeeding session shows a trend of increasing initial blood flow. With a treatments spaced two days apart, increased vascularity in the tissues of the trainee 46 occurred as a result of the enforced brain exercise and a long lasting effect was achieved. The patient recovered a sunny disposition toward the end of treatment. She then obtained her first job in 16 years. Similar brain blood flow results have been obtained with a stroke victim and several sufferers of ADD.

The following reference numerals are used on FIGS. 1 through 4:

| | |
|---|---|
| 8 | Generic detector |
| 10 | Preferred irradiation/detection subsystem |
| 12 | Electronics subassembly |
| 14 | Red light source |
| 18 | Infrared light source |
| 22 | Photo detector, photo amplifier or photo sensor |
| 26 | Flexible membrane or circuit |
| 30 | Band |
| 34 | Hook fastener |
| 38 | Loop fastener |
| 42 | Connector |
| 46 | Individual or trainee |
| 48 | Head |
| 50 | Forehead |
| 52 | First cable |
| 54 | Invention |
| 56 | Electronic processor |
| 70 | Second cable |
| 74 | Display module |
| 78 | Visual, audible, audio/visual or tactile display |

An apparatus for biofeedback of human central nervous system activity using radiation detection 54 has been described with reference to a several embodiments. In the process a method for biofeedback of human central nervous system activity using radiation detection has also been described. Other modifications and enhancements can be made without departing from the spirit and scope of the claims that follow.

What is claimed is:

1. A biofeedback method for allowing an individual to adjust the blood flow or oxygenation or metabolism of said individual's brain comprising:

a. administering energy to the brain of said individual; said energy designed to ascertain the blood flow or blood oxygenation or metabolism of said brain;

b. providing a detecting means for detecting radiation produced by said brain in response to said energy administration and producing a signal relating to said radiation; said signal providing a measure of said blood flow or blood oxygenation or tissue metabolism;

c. providing a display means for making a presentation of said signal so that said sensing and presentation permits control of said blood flow or blood oxygenation or tissue metabolism by said individual;

d. operatively connecting said detecting means to said display in a biofeedback system;

e. detecting said radiation and producing said signal on said display means;

f. presenting said signal on said display means;

g. arranging sensing of said presentation by said individual; and h. voluntarily controlling by said individual said blood flow or blood oxygenation or tissue metabolism in response to said presentation via biofeedback.

2. A biofeedback method as claimed in claim 1 further comprising the steps of:

a. providing a computing means for making calculations on said signal and outputting said calculations; said calculations designed to derive a representation of said blood flow or blood oxygenation or tissue metabolism from said signal;

b. operatively connecting said computing means between said detecting means and said display means;

c. making said calculations in said computing means; and d. outputting said calculations to said display means; whereby said presentation is made more meaningful to said individual.

3. The method of claim 1 further comprising the step of modifying said energy by an external field selected from the group consisting of electric, magnetic, or both.

4. A biofeedback method for allowing an individual to adjust an alterable characteristic of said individual's brain comprising the steps of:

a. providing a light source adapted to irradiate said individual's brain with light; the wavelength of said light selected to ascertain said alterable characteristic;

b. providing a radiation detector adapted for detecting radiation reflected and scattered by said individual's brain from said light source;

c. providing a processor capable of calculating a parameter of the radiation detected by said radiation detector; said parameter selected to represent said alterable characteristic;

d. providing a display which can display said parameter so that viewing said parameter on said display enables voluntary control of said alterable characteristic by said individual;

e. operatively interconnecting said light source, said radiation detector, said processor, and said display in a biofeedback system;

f. positioning said light source and said radiation detector about said individual's head so that said radiation detector will optimally detect light reflected and scattered by said individual's brain from said light source;

g. activating said light source and said radiation detector;

h. detecting radiation reflected and scattered by said individual's brain in said detector;

i. calculating said parameter in said processor;
j. outputting said parameter to said display;
k. arranging viewing of said display by said individual; and
l. voluntarily controlling by said individual said alterable characteristic in response to said display via biofeedback.

5. A biofeedback method as claimed in claim 4 further comprising the step of pulsing said light source.

6. A biofeedback method for allowing an individual to adjust an alterable characteristic of said individual's brain comprising the steps of:
   a. providing a red light source adapted to irradiate said individual's brain with red light of a wavelength of about 660 to 700 nm;
   b. providing an infrared light source adapted to irradiate said individual's brain with infrared light of a wavelength of about 800 to 1000 nm;
   c. providing a radiation detector adapted for detecting light reflected and scattered by said individual's brain from said red and infrared light sources;
   d. providing a processor capable of calculating a relationship between red and infrared light detected by said radiation detector; said relationship selected to represent said alterable characteristic;
   e. providing a display which can display said relationship so that viewing said relationship on said display means enables voluntary control of said alterable characteristic by said individual;
   f. operatively connecting said radiation detector to said processor and said processor to said display in a biofeedback system;
   g. positioning said red light source, said infrared light source and said radiation detector around said individual's head so that said radiation detector will optimally detect light reflected and scattered by said individual's brain from said red and infrared light sources;
   h. activating said red light source, said infrared light source and said radiation detector;
   i. detecting light reflected and scattered by said individual's brain from said red and infrared light sources in said radiation detector;
   j. calculating said relationship in said processor;
   k. outputting said relationship to said display;
   l. arranging viewing of said display by said individual; and
   m. voluntarily controlling by said individual said alterable characteristic in response to said display via biofeedback.

7. A biofeedback method as claimed in claim 6, additionally comprising the step of alternately activating said red light source and said infrared light source.

8. A biofeedback method as claimed in claim 6, further comprising the step of pulsing said light sources.

9. A biofeedback method as claimed in claim 6, further including the steps of:
   a. providing an attaching means for attaching said red light emitting means, said infrared light emitting means and said radiation detection means to said individual's head; and
   b. attaching said red light emitting means, said infrared light emitting means and said radiation detection means to said individual's head.

10. A method as claimed in claims 4, or 6, further comprising the step of eliminating interference with operation of said radiation detector from ambient light.

11. A biofeedback method for allowing an individual to adjust an alterable characteristic of said individual's brain comprising the steps of:
    a. providing a red light source adapted to irradiate said individual's brain with red light of a wavelength of about 660 to 700 nm;
    b. providing an infrared light source adapted to irradiate said individual's brain with infrared light of a wavelength of about 800 to 1000 nm;
    c. providing a radiation detector adapted for detecting radiation reflected and scattered by said individual's brain from said red and infrared light sources;
    d. providing a circuit operatively interconnecting said red light source, said infrared light source and said radiation detector;
    e. providing a processor capable of calculating a relationship between red and infrared light detected by said radiation detector; said relationship selected to represent said alterable characteristic;
    f. providing a display which can display said relationship for voluntary control by said individual;
    g. operatively connecting said processor to said circuit and said display in a biofeedback system;
    h. attaching said red light source, said infrared light source and said radiation detector to said individual's head so that said light sources are adjacent to each other, said radiation detector is 2 to 3.5 cm from said light sources, and ambient light is excluded from said radiation detector;
    i. activating said red light source, said infrared light source and said radiation detector;
    j. detecting radiation reflected and scattered by said individual's brain from said red and infrared light sources in said radiation detector;
    k. calculating said relationship;
    l. outputting said relationship to said display;
    m. arranging viewing of said display by said individual; and
    n. voluntarily controlling by said individual said alterable characteristic in response to said display via biofeedback.

12. A biofeedback method as claimed in claim 11, additionally comprising the step of alternately activating said red light source and said infrared light source.

13. A biofeedback method as claimed in claim 11, further comprising the step of pulsing said light sources.

14. A method for enabling an individual to adjust an alterable characteristic of said individual's brain comprising the steps of:
    a. providing a radiation detector adapted for detecting spectral components of radiant energy emanating from the brain of said individual;
    b. providing processing means capable of calculating a relationship between the spectral components of the output from said radiation detector;
    c. providing a sensory information means selected from the group consisting of sound, visual, and tactile means which can inform said individual of the detected relationship of the spectral components of the output of said processing means;
    d. providing a circuit operatively interconnecting said radiation detector, said processing means, and said sensory information means;
    e. including said individual in an operative feedback system comprising said radiation detector, said processing means, said sensory information means, and said circuit means for voluntary increase by said individual of blood flow, or blood oxygenation, or metabolism of said individual's brain;

f. operating said feedback system to inform said individual with said sensory information means;

g. voluntarily controlling by said individual said blood flow, or blood oxygenation, or metabolism in response to said information from said sensory information means via biofeedback.

15. The method of claim 14, further comprising the step of initially administering radioactive material in order to produce said radiant energy.

16. The method of claim 14, in which the radiant energy is light.

17. The method of claim 15 further comprising the step of modifying said radiant energy by an external field selected from the group consisting of electric, magnetic, or both.

18. The method of claim 17, in which radiant energy is light.

19. The method of claim 18, in which the wavelength of said light is selected to ascertain said individual's cerebral blood flow.

20. The method of claim 18, in which the wavelength of said light is selected to ascertain said individual's cerebral metabolism.

21. The method of claims 14, 15, 16, 17, 18, 19, or 20 in which said presenting step includes the step of making a calculation on said detected radiant energy.

* * * * *